United States Patent [19]

Schmid et al.

[11] Patent Number: 5,607,504
[45] Date of Patent: Mar. 4, 1997

[54] MULTIPLY COATED METALLIC LUSTER PIGMENTS

[75] Inventors: Raimund Schmid, Neustadt; Norbert Mronga, Dossenheim, both of Germany

[73] Assignee: BASF Aktiengesellschaft, Ludwigshafen, Germany

[21] Appl. No.: 348,245

[22] Filed: Nov. 28, 1994

[30] Foreign Application Priority Data

Oct. 21, 1994 [DE] Germany ............... 44 37 753.3

[51] Int. Cl.$^6$ ............................................. C09C 1/62
[52] U.S. Cl. ............... 106/403; 106/404; 106/436; 106/450; 106/453; 106/456
[58] Field of Search ............... 106/403, 404, 106/436, 450, 456, 453

[56] References Cited

U.S. PATENT DOCUMENTS

| 3,438,796 | 4/1969 | Hanke ............... 106/404 |
| 5,135,812 | 8/1992 | Phillips, et al. ........... 428/403 |
| 5,213,618 | 5/1993 | Souma et al. ............ 106/403 |
| 5,261,955 | 11/1993 | Nadkarni ............... 106/404 |
| 5,364,467 | 11/1994 | Schmid et al. ........... 106/403 |
| 5,401,306 | 3/1995 | Schmid et al. ........... 106/417 |

FOREIGN PATENT DOCUMENTS

| 0033457 | 8/1981 | European Pat. Off. . |
| 0045851 | 2/1982 | European Pat. Off. . |
| 0328906 | 8/1989 | European Pat. Off. . |
| 0338428 | 10/1989 | European Pat. Off. . |
| 0571836 | 12/1993 | European Pat. Off. . |
| 0579091A1 | 1/1994 | European Pat. Off. . |
| 0655486A3 | 5/1995 | European Pat. Off. . |
| 4319669 | 1/1994 | Germany . |
| 4313541A1 | 10/1994 | Germany . |

OTHER PUBLICATIONS

Database WPI, Derwent Publications Ltd., JP–A–06 093206, Apr. 5, 1994.

*Primary Examiner*—Helene Klemanski
*Attorney, Agent, or Firm*—Oblon, Spivak, McClelland, Maier & Neustadt, P.C.

[57] ABSTRACT

Luster pigments based on multiply coated plateletlike metallic substrates comprise at least one layer packet comprising
A) a colorless coating having a refractive index $n \leq 1.8$, and
B) a selectively absorbing coating having a refractive index $n \geq 2.0$
and also if desired additionally
C) an outer, colorless or selectively absorbing coating different than the layer (B) underneath.

9 Claims, No Drawings

MULTIPLY COATED METALLIC LUSTER PIGMENTS

The present invention relates to novel luster pigments based on multiply coated plateletlike metallic substrates with at least one layer packet comprising A) a colorless coating having a refractive index $n \leq 1.8$, and B) a selectively absorbing coating having a refractive index $n \geq 2.0$ and also if desired additionally C) an outer, colorless or selectively absorbing coating different than the layer (B) underneath.

The present invention further relates to the production of these pigments and to their use for coloring coatings, inks, including printing inks, plastics, glasses, ceramic products and decorative cosmetic preparations.

Luster effect pigments are used in many sectors of industry, for example in automotive coatings, decorative coating, plastics pigmentation, paints, printing inks, especially security printing inks, and cosmetics.

Their optical effect is based on the directed reflection of light at predominantly sheetlike, mutually parallel-oriented, metallic or strongly refractive pigment particles. Depending on the composition of the pigment platelets, interference, reflection and absorption phenomena create angle-dependent color and lightness effects.

Owing to their uncopyable optical effects, these pigments are increasingly gaining in important for production of forgeryproof security documents, such as banknotes, checks, check cards, credit cards, tax stamps, postage stamps, rail and air tickets, telephone cards, lottery tickets, gift vouchers, passes and identity cards.

Markings prepared with the luster effect: pigments and the absence of these markings or their alteration, for example in a color copy (disappearance of color flops and luster effects), are safely discernible by the unaided, naked eye and so make it easy to distinguish the original from the copy.

Metallic substrate luster pigments, having high hiding power, are also of particular interest for automotive coatings.

To date the following metallic luster pigments are known:
EP-A-33 457 describes iron oxide-coated aluminum pigments which have interesting golden to red hues at the luster angle. However, these pigments, like the aluminum pigments known from EP-A-338 428 or U.S. Pat. No. 5,261,955, which are coated with highly refractive metal oxides, specifically with reduced, blue titanium oxide or with colorless titanium dioxide and chromium or iron oxide or with a zirconium oxide layer containing iron(III) or cobalt(II) ions, show at steeper viewing angles a change from the particular, usually intense absorption color to achromatic.

There are also aluminum pigments exclusively coated with colorless, high refractive index metal oxides such as titanium dioxide or zirconium dioxide or else multiply with low refractive index silicon dioxide and high refractive index titanium dioxide, which aside from a strong metallic luster have only delicate interference colors (EP-A-338 428, U.S. Pat. No. 5,213,618, JP-A-93 206/1994).

Particularly interesting goniochromatic(ie. two-tone) pigments are obtained when, as described in EP-A-571 836 and German Patent Application P 44 05 492.0, metal oxide coatings (in particular high refractive index titanium dioxide and low refractive index silicon dioxide) are combined with metal coatings. Luster pigments having a similar layer sequence are known from U.S. Pat. Nos. 5,135,812 and 3,438,796. On account of their method of production, the central metal layer of these pigments is not completely enclosed on all sides by the outer layers.

However, these coloristically interesting pigments can cause fastness problems, especially in automotive coatings, owing to the outer metal coatings. Moreover, these pigments do not give all the color flops desired.

It is an object of the present invention to provide strong luster pigments which combine attractive coloristics and advantageous application properties.

We have found that this object is achieved by the luster pigments defined at the beginning.

We have also found a process for producing the luster pigments, which comprises coating the metallic substrate particles in succession with individual layers by gas phase decomposition of volatile metal compounds in the presence of oxygen and/or water vapor or wet-chemically by hydrolytic decomposition of organic metal compounds.

Finally, the present invention also provides for the use of the luster pigments for coloring paints, inks, including printing inks, plastics, glasses, ceramic products and decorative cosmetic preparations.

The metallic luster pigments of the present invention comprise a colorless, low refractive index coating (A) in combination with a selectively absorbing (ie. colored, but not black), high refractive index coating (B) and if desired an additional outer, colorless or selectively absorbing coating (C) which may have a low refractive index or a high refractive index but which is different from the layer (B) underneath, and may contain a plurality of identical or different combinations of (A)+(B); preferably, however, there is only one layer packet (A)+(B).

Coating (A) has a refractive index $n \leq 1.8$, preferably $\leq 1.6$, while coating (B) has a refractive index $n \geq 2.0$, preferably $\geq 2.4$.

Particularly preferred combinations of (A)+(B) generally have a refractive index difference of $\geq 0.4$, especially $\geq 0.8$.

Suitable materials for said coatings (A) and (B) are all substances which can be applied to the substrate particles in the form of a durable film and which have required optical properties. Of particular suitability are of course (especially for coating (B)) those materials which meet the application fastness requirements.

Preferred examples of the layer materials (A) and (B) are metal oxides which are colorless and have a low refractive index (A) or which are selectively absorbing and have a high refractive index (B).

Specific examples of suitable materials for coating (A) are silicon oxide, silicon oxide hydrate, aluminum oxide, aluminum oxide hydrate and mixtures thereof, preference being given to silicon oxide (hydrate).

Further materials suitable for, coating (A) include for example magnesium fluoride and aluminum phosphate.

High refractive index oxides suitable for coating (B) are preferably inherently selectively absorbing, especially iron(III) oxide ($\alpha$- and $\gamma$-$Fe_2O_3$, red) or else chromium(III) oxide (green), titanium(III) oxide (blue; generally present as a mixture with titanium oxynitrides and titanium nitrides owing to the usual preparation by reduction of $TiO_2$ with ammonia) and vanadium pentoxide (orange) and also mixtures thereof, but it is also possible to use colorless high refractive index oxides such as titanium dioxide and/or zirconium oxide which are "colored" with selectively absorbing colorants.

This "coloration" can be effected by incorporating the colorants into the metal oxide layer or by doping the metal oxide layer with selectively absorbing metal cations or by coating the metal oxide layer with a film containing the colorant.

Suitable colorants include for example inorganic and organic pigments, vat dyes and further organic dyes which are incorporable into a stable polymer film.

If desired, the "colored" coating (B) may additionally be stabilized by a layer (C).

Specific examples of suitable colorants include iron oxides, bismuth vanadate, colored spinels, nickel titanium yellow and cyano complexes of iron (Prussian blue); monoazo pigments (eg. products derived from acetoacetarylide derivatives or from β-naphthol derivatives), laked monoazo dyes, such as laked β-hydroxynaphthoic acid dyes, disazo pigments, fused disazo pigments, isoindoline derivatives, derivatives of naphthalene- or perylene-tetracarboxylic acid, anthraquinone pigments, thioindigo derivatives, azomethine derivatives, quinacridones, dioxazines, diketopyrrolopyrroles, pyrazoloquinazolones, phthalocyanine pigments and laked basic dyes, such as laked triarylmethane dyes.

The incorporation of pigments into the metal oxide layer (B) can simply be achieved by hydrolyzing an inorganic salt or alkoxide of the metal in aqueous or, for example, alcoholic solution and coprecipitating it with the pigment onto the substrate particles.

The doping of the metal oxide layer (B) with colored metal cations can be achieved in similar manner by entraining in the course of the oxide precipitation.

A suitable colorant-containing coating can be for example a colored polymer film which is applied by copolymerization of the monomers in the presence of dissolved dye or onto which a pigment is adsorbed or be a vat dye film precipitated onto the substrate particles by oxidation of the dissolved leuco form.

The methods mentioned have been repeatedly described in the patent literature and are therefore simple to carry out by one skilled in the art.

The luster pigments of the present invention may additionally contain a coating (C) as cover layer, which can serve for example to protect a $Ti_2O_3$ layer (B) or to improve the dispersibility.

Suitable for said coating (C) are colorless or selectively absorbing metal oxides, depending on whether or not the coloristics (ie. the color) of the pigment is to be additionally modified. The oxides can be not only of low refractive index but also of high refractive index. Examples are silicon oxide, silicon oxide hydrate, aluminum oxide, aluminum oxide hydrate, tin oxide, titanium dioxide, zirconium oxide, iron(III) oxide and chromium(III) oxide. Preference is given to silicon oxide (hydrate).

In the luster pigments of the present invention, the individual coatings generally have the following thicknesses:
(A) from 10 to 800 nm, preferably from 50 to 600 nm;
(B) from 1 to 500 nm, preferably from 10 to 150 nm;
(C) from 1 to 200 nm, preferably from 10 to 150 nm.

If a plurality (eg. 2, 3 or 4) of layer packets (A)+(B) are present, then coating (A) is preferably from 10 to 200 nm in thickness and coating (B) preferably from 10 to 50 nm in thickness.

Suitable metallic substrates for the luster pigments of the present invention include all metals and alloys in platelet form known for metallic effect pigments. Examples besides steel, copper and its alloys such as brass and bronzes include in particular aluminum and its alloys such as aluminum bronze.

Preference is given to aluminum flakes which are producible in a simple manner by stamping out of aluminum foil or by widely used atomization and grinding techniques.

Suitable aluminum pigments are produced for example by the Hall process by wet grinding in white spirit. The starting material is an atomized, irregular aluminum grit which is ball-milled in white spirit and in the presence of lubricant into plateletlike particles and subsequently classified.

Commercial products can be used. However, the surface of the aluminum particles should be Substantially free of fats or other coating media. These substances can to some extent be removed by solvent treatment or better, as described in DE-A-42 23 384, by oxidative treatment.

Furthermore, the metallic substrate particles may have been given a passivating treatment, ie. may have been given a coating which confers resistance especially against water, as known for example from German Patent Applications P 42 36 332.2 and 44 14 079.7.

The metallic substrate particles may if desired also be coated with metal oxide such as iron oxide or titanium oxide and therefore already possess a (weak) self-color due to interference effects with or without absorption. However, the metal oxide layer should not be too thick in order that the substrate particles may retain their "metallic coloristics".

Finally, it is also possible to use magnetizable aluminum platelets with an iron, cobalt, nickel or γ-$Fe_2O_3$ coating (German Patent Applications P 43 13 541.2 and 43 40 141.4).

The size of the substrate particles is not critical per se and can be adapted to the particular use. Generally the particles have average largest diameters from about 1 to 200 μm, in particular from about 5 to 100 μm, and thicknesses from about 0.1 to 5 μm, in particular around about 0.5 μm. Their specific free surface area (BET) is generally within the range from 0.1 to 5 $m^2$/g.

The luster pigments of the present invention combine altogether advantageous application properties (especially good fastness properties) especially with interesting coloristic properties. More particularly, they show color flops which are not obtainable with analogous luster pigments containing a metallic layer (B).

For instance, a pigment with aluminum/$SiO_2$/molybdenum layers in that order, which has a reddish golden interference color in reflected light, shows a greenish golden interference color at steeper viewing angles. A comparable pigment coated with $Fe_2O_3$ instead of molybdenum, by contrast, has a color flop from reddish golden toward deep red.

Thus, coating with iron oxide (B) gives luster pigments for the red hue region which, in the case of a thin iron oxide layer, show a color change from reddish golden→greenish golden, which color change changes with increasing $Fe_2O_3$ layer thickness to red-dish orange→deep red. It is thus possible, by varying the thickness of the $SiO_2$ and/or $Fe_2O_3$ layer, to obtain a whole palette of red hues which, depending on the viewing angle, flop toward greenish golden, neutral golden or reddish golden.

Coating with chromium oxide (B) correspondingly produces luster pigments giving a multiplicity of greens which flop toward blue or greenish golden or even red.

Blue coatings (B) ($MoO_x$, $WO_x$, $Ti_2O_3$) produce luster pigments with color flops in the violet or blue hue region.

In the novel process for producing the luster pigments of the present invention, the individual layers are applied by gas phase decomposition of suitable volatile metal compounds (chemical vapor deposition, CVD) or wet-chemically by hydrolytic decomposition of especially organic metal compounds.

Of course, the two methods can be combined in any desired way for producing the individual layers.

The metal oxide layers (A) are equally producible using the wet-chemical method and the CVD method, but the CVD method will usually be preferable, since the preferred metal oxide layers (B) are likewise particularly advantageously depositable from the gas phase. In that case there is no need for intermediately isolating and drying the pigment coated with (A).

In the wet-chemical process described in German Patent Application P 44 05 492.0, organic silicon and/or aluminum compounds in which the organic radicals are bonded to the metals via oxygen atoms are hydrolyzed in the presence of the substrate particles and of an organic solvent in which the metal compounds are soluble.

A multiplicity of organic solvents can be used for this; isopropanol is preferred.

Preferred examples of the metallic starting compounds are the acetyl acetonates and especially alkoxides, in particular $C_1$–$C_4$-alkoxides, eg. aluminum triisopropoxide and tetraethoxysilane.

The hydrolysis is preferably carried out in the presence of a base or acid as catalyst. Suitable for this purpose are not only for example alkali metal hydroxide solutions such as sodium hydroxide solution but also, in particular, aqueous ammonia solutions. Suitable acid catalysts include for example phosphoric acid and organic acids such as acetic acid and oxalic acid.

Water has to be present at least in the amount required stoichiometrically for the hydrolysis, but it is preferably present in from 2 to 100 times, especially from 5 to 20 times, the amount.

Based on the amount of water used, the rule is to add from 3 to 40% by volume, preferably from 5 to 30% by volume, of a 25% strength by weight aqueous ammonia solution.

As regards temperature management, it is advantageous to heat the reaction mixture to the reflux temperature step by step over a period from 10 to 48 h. If isopropanol is used as solvent, the mixture is preferably stirred for example initially at 40° C. for from 4 to 20 h, then at 60° C. for from 4 to 20 h and finally at 80° C. for from 2 to 8 h.

Technically, step a) of the production process according to the present invention is advantageously carried out as follows:

Substrate particles, organic solvent, water and catalyst (acid or preferably base, in particular for example an aqueous ammonia solution) are charged initially and the metal compound to be hydrolyzed is added pure or dissolved, for example in the form of a from 30 to 70, preferably from 40 to 60%, strength by volume solution in the organic solvent. If the metal compound is added in one step, the suspension is subsequently heated as described above with stirring. However, the metal compound can also be metered in continuously at elevated temperature, in which case water and ammonia can be included in the initial charge or likewise continuously metered in. On completion of the coating, the reaction mixture is cooled back down to room temperature.

To prevent agglomeration during the coating operation, the suspension can be subjected to a strong mechanical stress such as pumping, vigorous stirring or the action of ultrasound.

If desired, the coating step can be repeated one or more times. If the mother liquor has a milky appearance, it is advisable to replace it before a further coating operation is carried out.

The substrate particles coated with the layer (A) can be isolated in a simple manner by filtration, washing with organic solvent, preferably with the alcohols used as solvent, and subsequently drying (customarily at from 20° to 200° C. for from 2 to 24 h).

In the CVD process described in German Patent Application P 44 37 752.2, silanes which contain at least one alkanoyl radical are decomposed in the gas phase with water vapor and optionally oxygen in the presence of moving substrate particles.

Suitable silanes for this purpose conform in particular to the formula

where
R is alkyl, preferably $C_1$–$C_{10}$-alkyl, particularly preferably $C_1$–$C_6$-alkyl, which can be substituted by chlorine, which can be monounsaturated or polyunsaturated and whose carbon chain may be interrupted by one or more imino groups or oxygen atoms in the ether function; phenyl, which can be $C_1$–$C_2$-alkyl-substituted, or hydrogen;
X is alkoxy, preferably $C_1$–$C_6$-alkoxy, particularly preferably $C_4$-alkoxy, especially tert-butoxy;
Y is alkanoyloxy, preferably $C_2$–$C_3$-alkanoyloxy, particularly preferably acetoxy;
a is from 0 to 3, preferably from 0 to 2, particularly preferably 0;
b is from 0 to 3, preferably from 1 to 3, particularly preferably 2;
c is from 1 to 4, preferably from 1 to 3, particularly preferably 2,
the sum a+b+c=4 and the radicals R for a>1, the radicals X for b>1 and the radicals Y for c>1 can each be identical or different.

Of particular suitability are those silanes which at temperatures ≦600° C., for technical reasons especially ≦300° C., have a sufficiently high vapor pressure to ensure simple vaporization and are also easy to decompose with water vapor and/or air and depositable as oxide. Of course, it is also possible to use mixtures of different silanes.

Specific examples of preferred silanes include the following:

tetraacetoxysilane, methoxy-, ethoxy-, propoxy-, isopropoxy-, butoxy-, isobutoxy-, sec-butoxy- and tert-butoxy-triacetoxysilane, dimethoxy-, diethoxy-, dipropoxy-, diisopropoxy-, dibutoxy-, diisobutoxy-, di-sec-butoxy- and di-tert-butoxy-diacetoxysilane and trimethoxy-, triethoxy-, tripropoxy-, triisopropoxy-, tributoxy-, triisobutoxy-, tri-sec-butoxy- and tri-tert-butoxy-acetoxysilane and also silanes which contain different alkoxy radicals, eg. methoxyethoxydiacetoxysilane.

Very particular preference is given to di-tert-butoxydiacetoxysilane.

To carry out the CVD process, it is advisable, as generally the case for CVD processes, to use a fluidized bed reactor as described for example in EP-A-45 851. The substrate particles are heated in the reactor to the desired reaction temperature (generally from 100° to 600° C., preferably from 150° to 300° C.) under fluidization with an inert gas such as nitrogen, and silane and water vapor (and optionally oxygen) are then introduced with the aid of inert carrier gas streams (advantageously part-streams of the fluidizing gas) from upstream vaporizer vessels via separate nozzles.

To obtain homogeneous silicon oxide layers which will completely envelop the substrate particles in the form of a film, the silane concentration is advantageously held at ≦5% by volume, preferably ≦2% by volume, based on the total amount of gas in the reactor.

The amount of water vapor required for the decomposition depends on the concentration of the silane and should correspond at least to the amount stoichiometrically required for hydrolysis, but preference is given to an amount from 10 to 100 times that amount.

If the silane contains alkyl or phenyl substituents R, it is advisable to have oxygen present in the course of the decomposition if the deposited silicon oxide layer does not contain carbon residues which generally form when water vapor is used alone.

The metal oxide layers (B) are suitably applied, because of the high quality of the deposited layers, in particular by the CVD process, but if "colored" titanium dioxide or zirconium dioxide layers are to be used as coating (B), it can be more advantageous, depending on the "coloring method", to employ the wet-chemical option (eg. EP-A-328 906).

The CVD processes for depositing α-iron(III) oxide, chromium(III) oxide, titanium dioxide and titanium(III) oxide (in mixture with titanium oxynitrides and titanium nitrides) by oxidative decomposition of iron pentacarbonyl and chromium hexacarbonyl or hydrolytic decomposition of titanium tetraisopropoxide or titanium tetrachloride and subsequent reduction with ammonia are well known (EP-A-33 457, EP-A-338 428).

Wet-chemically, α-iron oxide and chromium oxide layers could be applied by hydrolytic decomposition of iron(III) salts such as iron(III) chloride and sulfate or chromium(III) chloride and subsequent conversion of the resulting hydroxide-containing layers by heat treatment into the oxide layers. Similarly, a titanium(III) oxide coating could be obtained by hydrolysis of titanium tetrachloride and subsequent reduction of the resulting titanium dioxide with gaseous ammonia.

The coating with a $\gamma$-$Fe_2O_3$ layer can be effected by the two CVD variants described in earlier German Patent Application P 43 40 141.4. Either iron pentacarbonyl can be decomposed in the presence of at least the stoichiometrically required amount, preferably with from 10 to 100 times the amount, of water vapor at from 180° to 250° C. to form magnetite, hydrogen and carbon monoxide and the deposited magnetite film subsequently oxidized at from 200° to 350° C. with air to give $\gamma$-$Fe_2O_3$, or iron pentacarbonyl can first be deposited by oxidative decomposition as α-$Fe_2O_3$, which is then reduced at from 200° to 400° C. with hydrogen-containing gases to form iron(II)-containing products and subsequently oxidized to $\gamma$-$Fe_2O_3$ as above.

Vanadium(V) oxide layers can finally be deposited by gas phase decomposition of vanadium oxychloride with water vapor.

If an outer metal oxide layer (C) is desired, it can be applied as described for the layers (A) and (B).

The production process of the present invention makes it possible to make the multiply coated luster pigments reproducibly in a simple manner in large amounts. The pigment particles obtained are completely enclosed and have individual coatings of high quality (homogeneous, filmlike).

The luster pigments of the present invention are advantageously suitable for many purposes, such as the coloring of plastics, glasses, ceramic products, decorative cosmetic preparations and in particular coatings and inks, including printing inks, especially security printing inks. All customary printing processes are possible, for example screen printing, intaglio printing, bronze printing, flexographic printing and offset printing.

The pigments of the present invention are also usable for these purposes with advantage in admixture with transparent and hiding white, colored and black pigments and also commercial luster pigments based on metal oxide-coated mica and metal pigments and plateletlike iron oxides.

EXAMPLES

Preparation of luster pigments according to the present invention

Example 1 a) In a round-bottom flask equipped with a reflux condenser and a stirrer, 200 g of aluminum powder (average particle diameter 60 μm, BET surface area 1.5 $m_2$/g) were slurried up in 1.5 l of isopropanol. Following addition of 600 ml of water and 40 ml of a 25% strength by weight aqueous ammonia solution, the suspension was heated to 60° C. with vigorous stirring. At the same time the metered addition was commenced of a mixture of 610 ml of isopropanol and 610 g of tetraethoxysilane (metering rate 130 ml/h). On completion of the metered addition (after about 10 h), the reaction mixture was stirred at 55° C. for a further 14 h.

After the suspension had been cooled down, the product was filtered off from the mother liquor, washed with isopropanol and dried at 80° C.

The coated aluminum powder had an $SiO_2$ content of 42.7% by weight and showed a slight greenish tinge.

b) For the subsequent coating with α-iron(III) oxide, 160 g of the dried product were heated in a fluidized bed reactor (described in EP-A-571 836) to 200° C. under fluidization with a total of 900 l/h of nitrogen. 300 l/h of the nitrogen was passed from a reservoir held at room temperature to carry 116 g of iron pentacarbonyl over 8 h into the reactor for decomposition there, through the simultaneous introduction of 200 l/h of air via a further nozzle, to α-$Fe_2O_3$ and carbon monoxide or dioxide.

The pigment obtained had an iron content of 12.4% by weight and, applied in a varnish, showed not only a virtually unchanged strong metallic luster but also a strong bluish red interference color which, at steeper viewing angles, flopped into a golden hue.

A pigment sample taken after addition of 87 g of $Fe(CO)_5$, which had an iron content of 9.2% by weight, showed a color flop from delicate red toward greenish golden.

Example 2 a) The same aluminum powder was coated by the method of Example 1a) with $SiO_2$ using a mixture of 550 ml of isopropanol and 550 g of tetraethoxysilane.

The coated aluminum powder had an $SiO_2$ content of 39.6% by weight and showed a slightly bluish tinge.

b) Example 1b) was then repeated using 210 g of the dried product, fluidizing with a total of 1000 l/h of nitrogen at 190° C., and supplying 175 g of $Fe(CO)_5$ (nitrogen stream 400 l/h) over 12 h.

The pigment obtained had an iron content of 14.9% by weight and, applied in a varnish, showed a strong metallic luster coupled with a strong golden interference color which, at steeper viewing angles, flopped toward deep red.

A pigment sample taken after 145 g of $Fe(CO)_5$ had been supplied, had an iron content of 12.3% by weight and showed a color flop from reddish golden toward neutral golden.

Example 3 a) The same aluminum powder was coated with $SiO_2$ by the method of Example 1a) using a mixture of 690 ml of isopropanol and 690 g of tetraethoxysilane.

The coated aluminum powder had an $SiO_2$ content of 52.4% by weight and a reddish shimmer.

b) Example 2b) was then repeated to coat 200 g of the dried product with α-$Fe_2O_3$ using 87 g of $Fe(CO)_5$ over 5 h.

The pigment obtained had an iron content of 11.3% by weight and, applied in a varnish, showed a strong metallic luster coupled with a deeply golden interference-color which, at steeper viewing angles, flopped into a weak red.

A pigment sample taken after 43.5 g of $Fe(CO)_5$ had been supplied had an iron content of 5.6% by weight and showed a color flop from weakly golden toward red.

Example 4 a) In a fluidized bed reactor of the same design as in Example 1b) but larger (diameter 16 cm, height 100 cm), 500 g of aluminum powder (average particle diameter 60 μm, specific surface area 1.5 m$^2$/g) were heated to 200° C. under fluidization with a total of 1420 l/h of nitrogen. Part of the fluidizing gas (400 l/h) was passed through a water reservoir temperature controlled to 50° C. To degrease the aluminum powder, 140 l of air were metered in via a further nozzle over 1 h.

From a further vaporizer reservoir, heated to 160° C., another 400 l/h of the fluidizing gas was used to carry a total of 775 ml of di-tert-butoxydiacetoxysilane in 25 ml portions over 20.5 h into the reactor for decomposition there into $SiO_2$, which deposits on the aluminum, tert-butanol and acetic acid.

A pigment sample had an $SiO_2$ content of 25.0% by weight and a virtually unchanged metallic appearance.

b) For the subsequent coating with α-$Fe_2O_3$, the fluidized bed temperature was adjusted to 190° C., the silane reservoir was replaced by a $Fe(CO)_5$ reservoir held at room temperature. Using a total of 1600 l/h of nitrogen as fluidizing gas, 130 g of $Fe(CO)_5$ were transported over 8 h with a nitrogen stream of 400 l/h into the reactor for oxidative decomposition there with 300 l/h of air introduced via the water reservoir.

The pigment obtained had an iron content of 5.0% by weight and, applied in a varnish, showed a virtually unchanged strong metallic luster coupled with a deep reddish golden interference color which, at steeper viewing angles, flopped into a greenish golden hue.

Example 5 a) The same aluminum powder was coated with $SiO_2$ by the method of Example 1a) using a mixture of 730 ml of isopropanol and 730 g of tetraethoxysilane.

The coated aluminum powder had an $SiO_2$ content of 49.0% by weight and a greenish shimmer.

b) 250 g of the dried product were then coated with chromium(III) oxide in the fluidized bed reactor of Example 1b) under fluidization with a total of 1000 l/h of nitrogen at 220° C. by the addition of 50.6 g of chromium hexacarbonyl from a reservoir temperature controlled to 70° C. (400 l/h of the nitrogen) and simultaneous introduction of 200 l/h of air, over 20 h.

The pigment obtained had a chromium content of 4.3% by weight and, applied in a varnish, showed a strong metallic luster coupled with a deep green interference color which, at steeper viewing angles, flopped toward red.

We claim:

1. Luster pigments based on multiply coated platelet-shaped metallic substrates with at least one layer packet comprising
   A) a first colorless coating having a refractive index $n \leq 1.8$, and
   B) a second selectively absorbing coating having a refractive index $n \leq 2.0$, applied upon said first coating,
   and optionally
   C) a third, outer, colorless or selectively absorbing coating different from said second coating and applied upon said second coating, and wherein coating (B) consists essentially of selectively absorbing oxides selected from the group consisting of iron (III) oxide, chromium (III) oxide, vanadium (V) oxide, titanium (III) oxide or mixtures thereof, or of colorless oxides selected from the group consisting of titanium dioxide, zirconium oxide or mixtures thereof, which have been colored with the aid of selectively absorbing colorants.

2. Luster pigments as claimed in claim 1 wherein coating (A) is a layer consisting essentially of a colorless metal oxide having a low refractive index.

3. Luster pigments as claimed in claim 1 wherein coating (B) is a layer consisting essentially of a selectively absorbing metal oxide having a high refractive index or is a layer which consists essentially of a colorless metal oxide having a high refractive index and in which selectively absorbing colorants are incorporated or which has been provided with a coating containing these colorants.

4. Luster pigments as claimed in claim 1 wherein coating (A) consists essentially of silicon oxide, silicon oxide hydrate, aluminum oxide, aluminum oxide hydrate, or mixtures thereof.

5. Luster pigments as claimed in claim 1 wherein coating (C) consists essentially of silicon oxide, silicon oxide hydrate, aluminum oxide, aluminum oxide hydrate, titanium dioxide, zirconium oxide, iron (III) oxide, chromium (III) oxide, or mixtures thereof.

6. Luster pigments according to claim 1 wherein there is only one layer packet (A) and (B).

7. Luster pigments according to claim 1 wherein the metallic substrate consists essentially of passivated or unpassivated aluminum platelets.

8. A process for producing luster pigments as claimed in claim 1, which comprises coating the metallic substrate particles in succession with individual layers by gas phase decomposition of volatile metal compounds in the presence of oxygen, water vapor, or a mixture thereof, or wet-chemically by hydrolytic decomposition of organic metal compounds.

9. A method for coloring paints, inks, plastics, glasses, ceramic products or decorative cosmetic preparations, which comprises adding thereto the luster pigments of claim 1.

* * * * *

UNITED STATES PATENT AND TRADEMARK OFFICE
CERTIFICATE OF CORRECTION

PATENT NO. : 5,607,504

DATED : March 4, 1997

INVENTOR(S) : Raimund SCHMID, et al.

It is certified that error appears in the above-identified patent and that said Letters Patent is hereby corrected as shown below:

Col. 10, line 8, "$n \leq 2.0$" should read --$n \geq 2.0$--.

Signed and Sealed this

Twenty-second Day of July, 1997

Attest:

BRUCE LEHMAN

*Attesting Officer*　　　*Commissioner of Patents and Trademarks*